(12) United States Patent
Lu

(10) Patent No.: US 6,493,584 B1
(45) Date of Patent: Dec. 10, 2002

(54) IMPLANTABLE CARDIAC STIMULATION DEVICE AND METHOD WHICH DISCRIMINATES BETWEEN NOISE AND CARDIAC ACTIVITY

(75) Inventor: Richard Lu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 223 days.

(21) Appl. No.: 09/658,051

(22) Filed: Sep. 8, 2000

(51) Int. Cl.$^7$ ................................................ A61N 1/362
(52) U.S. Cl. ............................ 607/9; 128/901; 600/515
(58) Field of Search ........................... 607/9, 14, 4, 5; 128/901; 600/515, 518

(56) References Cited

U.S. PATENT DOCUMENTS

| | | |
|---|---|---|
| 4,712,555 A | 12/1987 | Thornander et al. |
| 4,788,980 A | 12/1988 | Mann et al. |
| 4,799,493 A | 1/1989 | DuFault |
| 4,940,052 A | 7/1990 | Mann et al. |
| 4,944,298 A | 7/1990 | Sholder |
| 4,960,123 A * | 10/1990 | Maker ........................ 128/901 |
| 5,466,254 A | 11/1995 | Helland |
| 5,817,134 A | 10/1998 | Greenhut et al. |
| 5,868,680 A | 2/1999 | Steiner et al. |
| 5,871,507 A | 2/1999 | Obel et al. |
| 5,967,995 A | 10/1999 | Shusterman et al. |

* cited by examiner

Primary Examiner—George R. Evanisko

(57) ABSTRACT

An implantable cardiac stimulation device discriminates between noise and an arrhythmia sensed in a heart. A first sensing circuit generates a first signal representing electrical activity sensed in a first location of the heart and a second sensing circuit generates a second signal representing electrical activity sensed in a second location of the heart. The first and second locations are spaced apart and located in respective different corresponding chambers or the same chambers of the heart. A comparison circuit then compares the first and second signals to provide a comparison factor. A control circuit then determines from the comparison factor if noise is sensed or if an arrhythmia is being sensed.

30 Claims, 3 Drawing Sheets

IMPLANTABLE CARDIAC STIMULATION DEVICE AND METHOD WHICH DISCRIMINATES BETWEEN NOISE AND CARDIAC ACTIVITY

FIELD OF THE INVENTION

The present invention generally relates to an implantable cardiac stimulation device. The present invention more particularly relates to such a device and a method, which discriminates between noise sensing and arrhythmia detection.

BACKGROUND OF THE INVENTION

Implantable cardiac stimulation devices are well known in the art. They include implantable pacemakers which provide stimulation pulses to a heart, which would normally or otherwise beat too slowly or at an irregular rate, to beat at a controlled normal rate. They also include defibrillators which detect when the atria and/or the ventricles of the heart are in fibrillation and apply cardioverting or defibrillating electrical energy to restore the heart to a normal rhythm. Implantable cardiac stimulation devices may also include the combined functionalities of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation therapy when it is required.

Unfortunately, noise within the device sensing channel bandwidth can interfere with the sensing function. In a pacemaker, for example, noise can be mistaken by the device for a legitimate cardiac event causing stimulation inhibition. This can lead to long periods of a systole. In an implantable defibrillator, noise can cause mistaken diagnosis of fibrillation resulting in inappropriate therapy delivery.

Unneeded defibrillation therapy to the atria can cause unwarranted discomfort to a patient, and hence should be avoided. However, unneeded defibrillation therapy to the ventricles can be much worse. Generally, patients suffering from an episode of ventricular fibrillation are rendered unconscious before therapy is delivered. Even though the defibrillation shocks are of relatively high energy, to assure defibrillation, they are not felt by the patient. However, if ventricular fibrillation is inappropriately detected and the patient is conscious when the unneeded therapy is delivered, the therapy could be traumatic to the patient. Even worse, inappropriate shocks can induce ventricular fibrillation to create a potentially life threatening situation. As a result, it is most desirable, if not essential, that such unnecessary ventricular defibrillation therapy or shocks be avoided. The present invention provides an implantable cardiac stimulation device and method capable of discriminating between sensed noise and cardiac tachyarrhythmias to avoid the delivery of unnecessary defibrillation therapy.

SUMMARY OF THE INVENTION

The present invention provides an implantable cardiac stimulation device and method, which discriminates between sensed noise and cardiac arrhythmias. The noise discrimination contemplated by the present invention is based upon the fact that noise interference, sensed at one location of the heart will be closely correlated to the noise from the same source sensed at another distant location of the heart. However, during an arrhythmia, such as fibrillation, localized cardiac electrical activity sensed at one location of the heart will not find good correlation with localized cardiac electrical activity sensed at the other distant location of the heart.

In accordance with the broader aspects of the present invention, a first sensing circuit senses electrical activity at a first location of the heart to generate a first signal and a second sensing circuit senses electrical activity at a second location of the heart to generate a second signal. The first and second locations are spaced apart and may be in a common chamber or in respective different corresponding chambers such as the right atrium and the left atrium or the right ventricle and the left ventricle. As used herein, the recitation of "in a chamber" is meant to include sensing within a given chamber as well as sensing from a location closely adjacent to and in electrical contact with the given chamber. Hence, the sensing of electrical activity in the left ventricle or in the left atrium includes sensing electrical activity with an electrode positioned in the coronary venous system of the heart adjacent the respective chamber.

The first and second signals are compared by a comparison circuit as implemented, for example, in a processor, to provide a comparison factor. A control circuit determines from the comparison factor if noise is being sensed or if an arrhythmia is being sensed.

If it is determined that noise is being sensed, the implantable cardiac stimulation device may be caused to revert to a noise reversion mode. However, if it is determined that an arrhythmia is being sensed, the implantable cardiac stimulation device may be caused to change operating state to enter a therapy mode of applying cardioversion therapy to the subject chambers. The cardioversion therapy may include, for example, high or low energy defibrillation therapy or anti-tachyarrhythmia pacing therapy. The therapy mode may first include arrhythmia confirmation by an arrhythmia detector before defibrillation or cardioversion.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
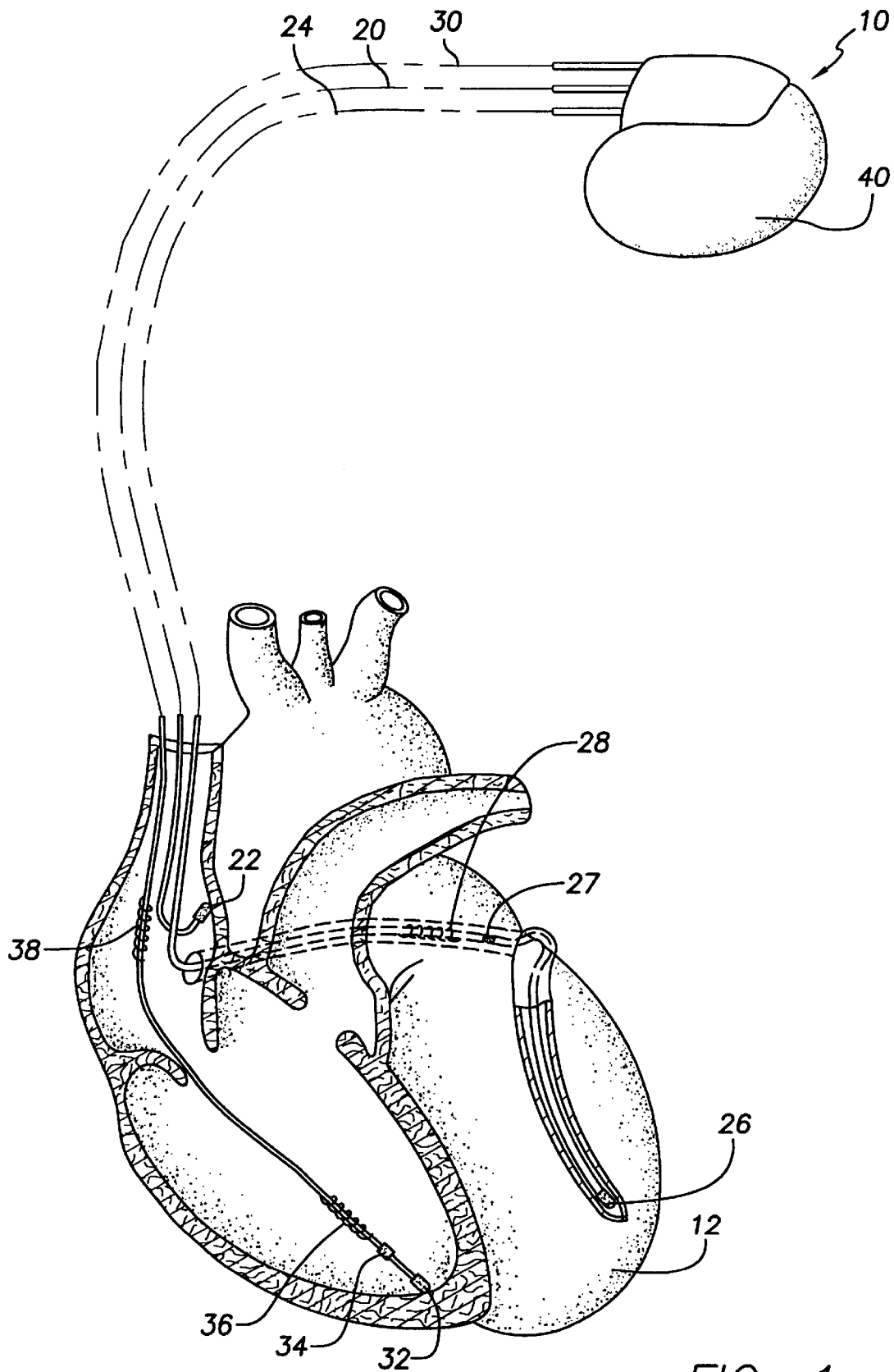
FIG. 1 is a simplified diagram illustrating an implantable stimulation device embodying the present invention in electrical communication with at least three leads implanted into a patient's heart for delivering multi-chamber stimulation and shock therapy.

As shown in FIG. 1, there is a stimulation device 10 embodying the present invention in electrical communication with a patient's heart 12 by way of three leads, 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et al.), which is a continuation-in-part of U.S. patent application Ser. No. 09/196,898 (now abandoned); and U.S. patent No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
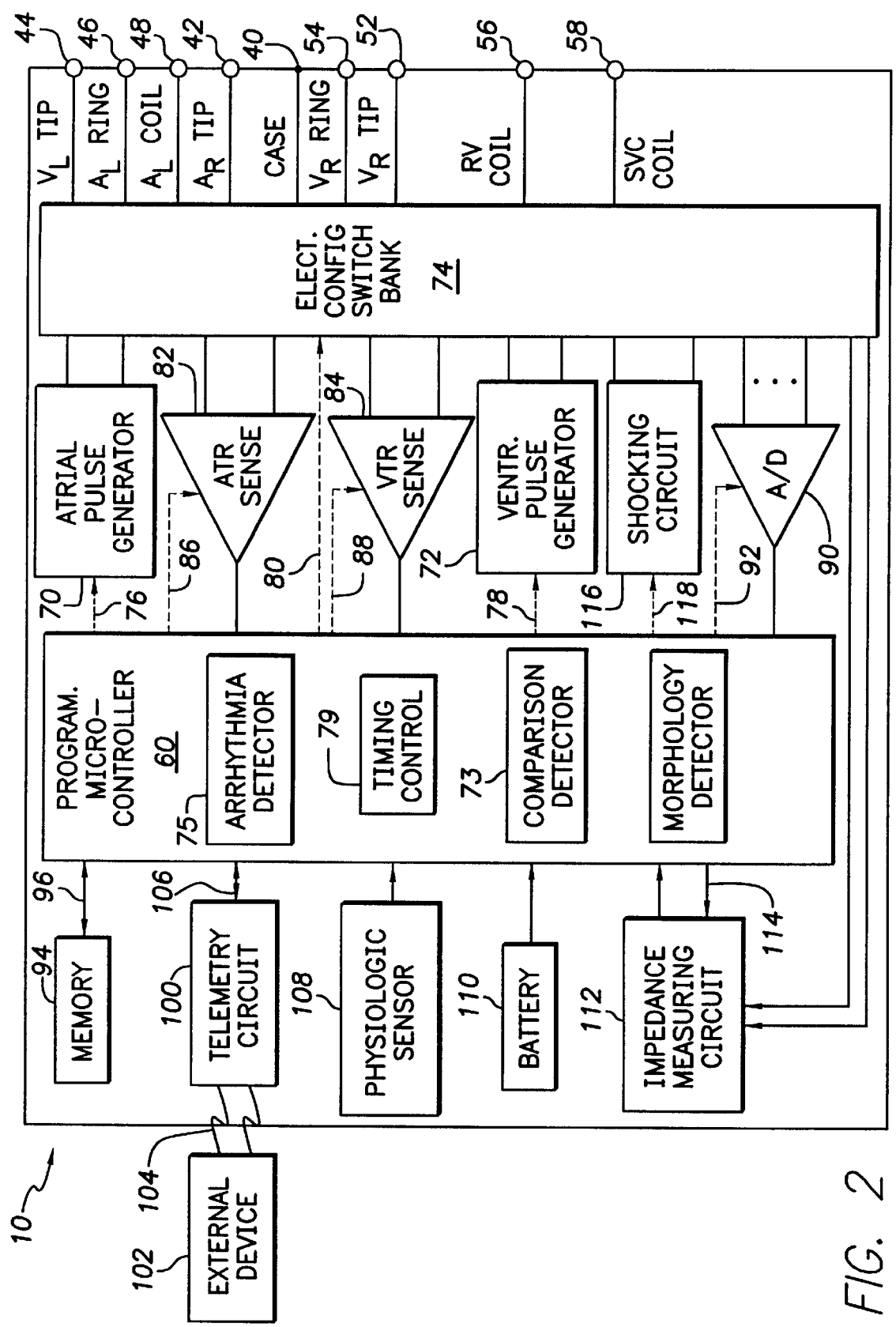
FIG. 2 is a functional block diagram of the device of FIG. 1 illustrating the basic elements of the device which can provide cardioversion, defibrillation and pacing stimulation in four chambers of the heart as well as noise discrimination in accordance with a preferred embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" electrode configurations. The housing 40 may further be used as a return electrode alone or in combination with one of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial tip electrode 22.

To achieve left chamber sensing, pacing and shocking, the connector includes at least a left ventricular tip terminal 44, a left atrial ring terminal 46, and a left atrial shocking terminal 48, which are adapted for connection to the left ventricular tip electrode 26, the left atrial tip electrode 27, and the left atrial coil electrode 28, respectively.

To support right chamber sensing, pacing and shocking, the connector further includes a right ventricular tip terminal 52, a right ventricular ring terminal 54, a right ventricular shocking terminal 56, and an SVC shocking terminal 58, which are adapted for connection to the right ventricular tip electrode 32, right ventricular ring electrode, 34, the RV coil electrode 36, and the SVC coil electrode 38, respectively.

As will be seen subsequently, the noise discrimination of this embodiment includes the sensing of electrical activity at first and second spaced apart locations of the heart. The first and second locations may be in a common chamber or in respective different corresponding chambers such as the right ventricle and the left ventricle or the right atrium and the left atrium. Further, the sensing of electrical activity "in" a chamber is meant to include both sensing in a chamber as well as sensing in a location closely adjacent to and in electrical contact with the given chamber. Hence, for example, sensing in the left ventricle is meant to include sensing with, for example, electrode 26 in the coronary sinus adjacent the left ventricle and sensing in the left atrium is meant to include sensing with, for example, electrode 27 in the coronary sinus adjacent the left atrium.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et al.), the state-machine of U.S. Pat. Nos. 4,712,555 (Sholder) and 4,944,298 (Sholder). For a more detailed description of the various timing intervals used within the stimulation device and their inter-relationship, see U.S. Pat. No. 4,788,980 (Mann et al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74 for sensing electrical activity in each of the four chambers of the heart and providing a corresponding electrical signal. Accordingly, the atrial and ventricular sensing circuits, 82 and 84, may include dedicated sense amplifiers, multiplexed amplifiers, or shared amplifiers. The switch bank 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 84, as is known in the art.

The microcontroller 60 further includes a comparison detector 73. In accordance with the present invention, the comparison detector 73 compares a first signal representing electrical activity sensed in one location of the heart, such as in the right ventricle or right atrium, with a second signal representing electrical activity sensed in another location of the heart such as the left ventricle or left atrium, respectively. The comparison results in a comparison factor used by the microcontroller 60 in determining if noise has been sensed instead of an arrhythmia.

For arrhythmia detection, the arrhythmia detector 75 of device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, low energy defibrillation shocks or high energy defibrillation shocks, collectively referred to as "tiered therapy").

If the comparison factor provided by the comparison detector 73 is less than a given factor, it will be determined that noise has been sensed. In this event, in accordance with the preferred embodiment, the microcontroller reverts the device to a noise reversion mode of, for example, a type well known in the art, wherein the device 10 reverts to asynchronous fixed-rate pacing for as long as the noise is sensed.

If the comparison factor is greater than the given factor, the response of the microcontroller may depend on the chambers in which activity was sensed to provide the comparison factors. For example, if the compared signals resulted from sensing in the right and left atria, the microcontroller may determine that a tachyarrhythmia is or might be present. In this event, the microcontroller may cause the device to change states to dissociate the atria from the ventricles by pacing the ventricles only for a time. During this time, the arrhythmia detector may detect for or confirm the presence of an atrial arrhythmia such as atrial fibrillation in a manner as previously described. If atrial fibrillation is detected, the device may then deliver defibrillation or cardioverting therapy to the atria in a manner to be described subsequently.

In the event that the compared signals resulted from sensing in the right and left ventricles, the microcontroller may take more affirmative action since the heart may be in ventricular fibrillation, a life threatening arrhythmia. Here, the microcontroller preferably commands ventricular defibrillation therapy. Alternatively, the arrhythmia detector may first be called upon to detect or confirm the ventricular fibrillation before defibrillation therapy is administered. Ventricular defibrillation therapy offered by the device 10 will also be described subsequently.

As will be appreciated by those skilled in the art, the given factor value may vary depending on many factors such as the chambers being sensed, the sampling rate, the sampling period, the patient's own physiological characteristics, and the method by which the comparison factor is derived, such as be correlation or the comparison factor equation to be described subsequently. However, by way of example only, and in accordance with this embodiment, the given factor may be on the order of 0.5 mV for atrial sensing and 10 mV for ventricular sensing.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 employs lithium/silver vanadium oxide batteries, as is true for most (if not all) such devices to date.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 by a control signal 114. The impedance measuring circuit 112 is not critical to the present invention and is shown for only completeness.

It is the primary function of the device 10 to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as common).

Cardioversion shocks are generally considered to be of low to moderate energy level (so as to minimize pain felt by the patient and to conserve current drain), and/or synchronized with an R-wave and/or pertaining to the treatment of tachycardia. Defibrillation shocks are generally of moderate to high energy level (I.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
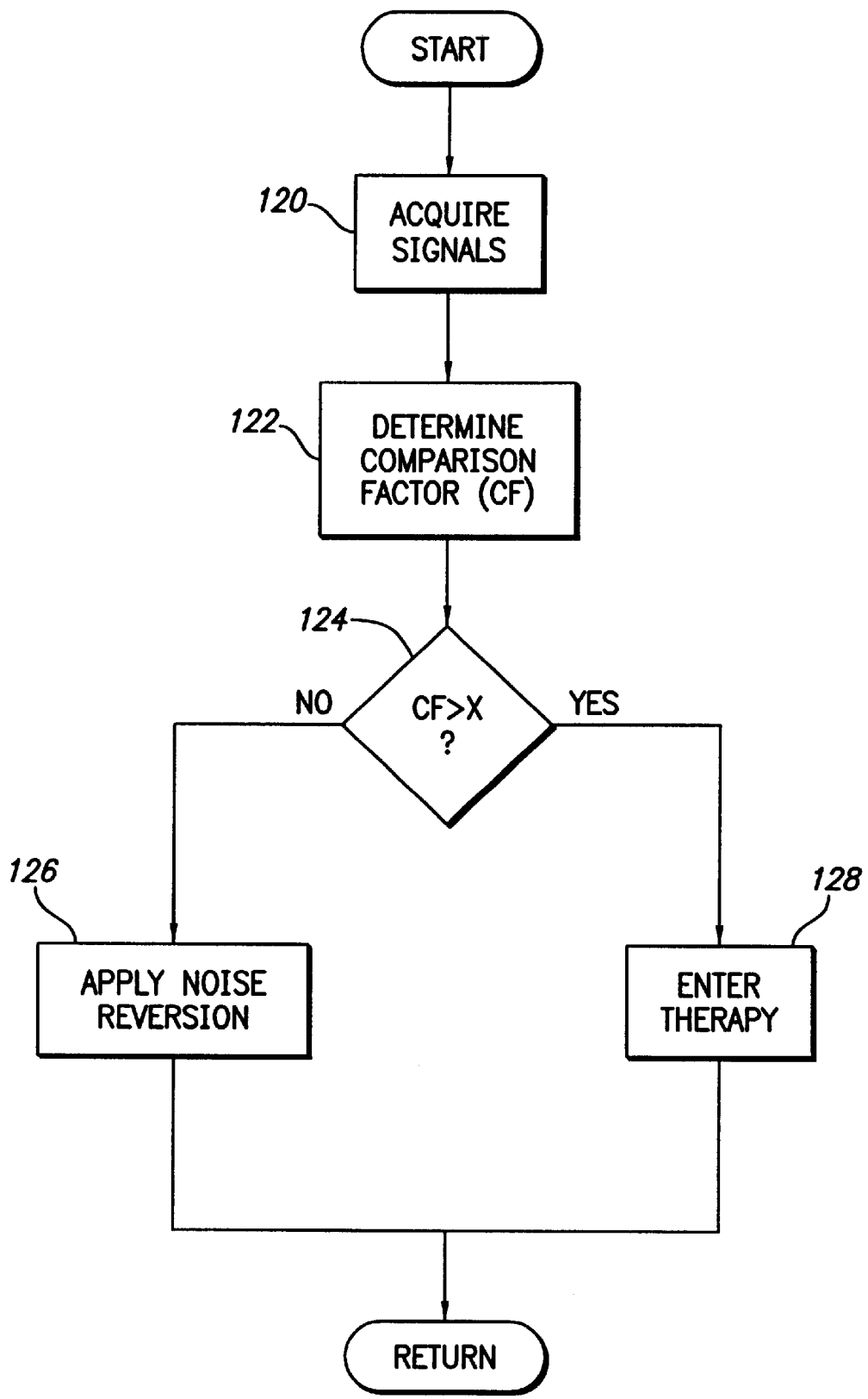
FIG. 3 is a flow chart describing an overview of the operation of one embodiment of the present invention.

In FIG. 3, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates with an activity block 120 wherein electrical signals preferably from corresponding right and left heart chambers are acquired and stored in memory 94. The electrical signal may represent the electrical activity sensed in the corresponding chambers over a cardiac cycle of the heart. The process then advances to activity block 122 wherein the signals acquired in activity block 120 are compared by the microcontroller 60 to provide a comparison factor (CF). The comparison factor may be determined using the formula:

$$CF = \frac{\sum_{i=1}^{n} |LC_i - RC_i|}{n}$$

wherein
$LC_i$ is signal sample $i^{th}$ acquired from the left heart chamber,
$RC_i$ is signal sample $i^{th}$ acquired from the right heart chamber, and
n is the number of samples.

The process then advances to decision block 124 wherein the microcontroller determines if the comparison factor (CF) determined in activity block 122 is greater than a given factor (X). If it is not, meaning that CF is less than X, the microcontroller 60 determines that noise has been sensed and hence, in accordance with activity block 126, reverts the device 10 to a noise reversion mode of the type, for example, as previously described.

If however, it is determined in decision block 124 that CF is indeed greater that X, the microcontroller 60 will cause a state change in the device 10 as an arrhythmia is or may be present. The state change, as represented in activity block 128 is preferably a therapy state of one of the types previously described. To that end, if an atrial arrhythmia is present, the device may mode switch (e.g., from DDDR to DDIR) to pace the ventricles only for a time sufficient to confirm atrial fibrillation and then deliver atrial anti-tachycardia pacing, defibrillation or cardioverting therapy. If a ventricle arrhythmia is present, the device may either directly apply ventricular anti-tachycardia pacing, defibrillating therapy or first confirm the presence of ventricular fibrillation.

While the comparison factor alone may be of sufficient sensitivity and specificity to permit defibrillation based thereon alone, the comparison factor is preferably one factor utilized by the device together with other forms of arrhythmia detection as, for example, rate detection as previously described, either performed prior to noise discrimination or thereafter, to justify delivery of defibrillation therapy. Hence, activity block 128 is contemplated as representing either the direct application of defibrillation therapy with confirmation prior to noise discrimination or defibrillation therapy after original detection.

The noise discrimination process of FIG. 3 may be initiated on a continued basis. Alternatively, it may be initiated in response to detection of an arrhythmia by the arrhythmia detector 75 to affirm that the arrhythmia detection was based upon sensed actual cardiac activity instead of noise.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device that discriminates noise from a cardiac arrhythmia of a heart comprising:
   a first sensing circuit that generates a first signal representing electrical activity sensed at a first location of the heart;
   a second sensing circuit that generates a second signal representing electrical activity sensed at a second location of the heart, the first location being spaced from the second location and the first and second locations being in a common chamber or respective corresponding chambers;
   a comparison circuit that determines a difference between the first and second signals to provide a comparison factor; and
   a control circuit responsive to the comparison factor that discriminates noise from said cardiac arrhythmia.

2. The device of claim 1 wherein the control circuit is programmed with a noise reversion mode and causes the device to revert to the noise reversion mode when noise is discriminated.

3. The device of claim 1 wherein the device has plural operating states and wherein the control circuit causes the device to change operating states upon failing to discriminate noise.

4. The device of claim 1 further including a cardioverting circuit that is operative to deliver cardioverting therapy and wherein the control circuit causes the cardioverting circuit to deliver cardioverting therapy to the heart upon failing to discriminate noise.

5. The device of claim 1 wherein the first and second locations are in the right atrium and the left atrium respectively.

6. The device of claim 5 further including a first electrode coupled to the first sensing circuit and adapted to be positioned in the right atrium and a second electrode coupled to the second sensing circuit and adapted to be positioned in the coronary sinus in electrical contact with the left atrium.

7. The device of claim 1 wherein the first and second locations are in the right ventricle and the left ventricle respectively.

8. The device of claim 7 further including a first electrode coupled to the first sensing circuit and adapted to be positioned in the right ventricle of the heart and a second electrode coupled to the second sensing circuit and adapted to be positioned in the coronary sinus in electrical contact with the left ventricle.

9. The device of claim 1 wherein the first and second locations are in one of the atria.

10. The device of claim 1 wherein the first and second locations are in one of the ventricles.

11. An implantable cardiac stimulation device that discriminate noise and arrhythmia of a heart comprising:
    sensing means for sensing electrical activity at first and second locations of the heart and generating first and second signals respectively, the first and second locations being spaced apart and being in a common chamber or first and second corresponding chambers, respectively;
    comparing means for comparing the first and second signals to provide a comparison factor; and
    discrimination means responsive to the comparison factor for discriminating noise from said arrythmia.

12. The device of claim 11 wherein the discrimination means includes means for causing the device to revert to a noise reversion mode upon determining that noise is discriminated.

13. The device of claim 11 wherein the discrimination means includes means for causing the device to change operating state upon determining that an arrhythmia is discriminated.

14. The device of claim 11 further including cardioverting means for delivering cardioverting therapy to the heart responsive to the discrimination means determining that an arrhythmia is discriminated.

15. The device of claim 11 wherein the first and second locations are the right atrium and the left atrium.

16. The device of claim 15 further including first electrode means coupled to the sensing means and adapted to be positioned in the right atrium and second electrode means coupled to the sensing means and adapted to be positioned in the coronary sinus in electrical contact with the left atrium.

17. The device of claim 11 wherein the first and second locations are the right ventricle and the left ventricle.

18. The device of claim 17 further including a first electrode means coupled to the sensing means and adapted to be positioned in the right ventricle of the heart and second electrode means coupled to the sensing means and adapted to be positioned in the coronary sinus in electrical contact with the left ventricle.

19. The device of claim 11 wherein the first and second locations are in one of the atria.

20. The device of claim 11 wherein the first and second locations are in of the ventricles.

21. In an implantable cardiac stimulation device, a method of discriminating noise and arrhythmia of a heart, the method including the steps of:

sensing electrical activity at first and second locations of the heart and generating first and second signals respectively, the first and second locations being spaced apart and being in a common chamber or first and second corresponding chambers, respectively;

comparing the first and second signals to provide a comparison factor; and in response to the comparison factor.

22. The method of claim 21 including the further step of causing the device to revert to a noise reversion mode when noise is discriminated.

23. The method device of claim 21 including the further step of causing the device to change operating state when an arrhythmia is discriminated.

24. The method of claim 21 wherein the device includes a cardioverting circuit and wherein the method further includes the step of causing the cardioverting circuit to deliver cardioverting therapy to the heart when an arrhythmia is discriminated.

25. The method of claim 21 wherein the first chamber is the right atrium and the second chamber is the left atrium.

26. The method of claim 25 wherein the sensing step includes sensing with a first electrode positioned in the right atrium and sensing with a second electrode positioned in the coronary sinus in electrical contact with the left atrium.

27. The method device of claim 21 wherein the first chamber is the right ventricle and the second chamber is the left ventricle.

28. The method of claim 27 wherein the sensing step includes sensing with a first electrode positioned in the right ventricle of the heart and sensing with a second electrode positioned in the coronary sinus in electrical contact with the left ventricle.

29. The method of claim 21 wherein the first and second locations are in one of the atria.

30. The method of claim 21 wherein the first and second locations are in one of the ventricles.

\* \* \* \* \*